US 8,052,663 B2

(12) United States Patent
Härsjö

(10) Patent No.: US 8,052,663 B2
(45) Date of Patent: Nov. 8, 2011

(54) MALE INCONTINENCE PRODUCT

(75) Inventor: Maria Härsjö, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 318 days.

(21) Appl. No.: 12/084,888

(22) PCT Filed: Nov. 22, 2005

(86) PCT No.: PCT/SE2005/001751
§ 371 (c)(1),
(2), (4) Date: May 12, 2008

(87) PCT Pub. No.: WO2007/061341
PCT Pub. Date: May 31, 2007

(65) Prior Publication Data
US 2010/0228217 A1 Sep. 9, 2010

(51) Int. Cl.
*A61F 5/44* (2006.01)
(52) U.S. Cl. .................. 604/349; 604/385.01
(58) Field of Classification Search .......... 604/346–349, 604/354–355, 385.01, 385.03, 386–387, 604/389–390
See application file for complete search history.

(56) References Cited

U.S. PATENT DOCUMENTS

| | | | |
|---|---|---|---|
| 4,324,246 A * | 4/1982 | Mullane et al. | 604/366 |
| 4,505,707 A | 3/1985 | Feeney | |
| 4,690,680 A * | 9/1987 | Higgins | 604/386 |
| 5,486,168 A | 1/1996 | Runeman et al. | |
| 5,558,734 A | 9/1996 | Sherrod et al. | |
| 6,565,548 B1 | 5/2003 | Glaug et al. | |

FOREIGN PATENT DOCUMENTS

| | | |
|---|---|---|
| DE | 296 02 160 U1 | 5/1996 |
| DE | 298 21 849 U1 | 3/1999 |
| DE | 100 45 440 A1 | 12/2001 |
| JP | S61-62462 A | 3/1986 |
| JP | H02-25228 U | 2/1990 |
| JP | 2003-500164 A | 1/2003 |
| RU | 2 090 170 | 9/1997 |
| WO | WO 91/11163 | 8/1991 |
| WO | WO 92/01431 A1 | 2/1992 |
| WO | WO 97/22316 A1 | 6/1997 |
| WO | WO 2006/071161 A1 | 7/2006 |

OTHER PUBLICATIONS

PCT/ISA/210.
PCT/ISA/237.

(Continued)

*Primary Examiner* — Michele M Kidwell
(74) *Attorney, Agent, or Firm* — Buchanan Ingersoll & Rooney PC

(57) ABSTRACT

The present invention concerns a male incontinence guard 10. The guard is divided by a transverse dividing line 25 into a front region 18 with a front transverse edge 20 and a rear region 22 with a rear transverse edge 24. The guard 10 tapers towards the rear transverse edge 24. The garment-facing surface 26 of the guard 10 comprises a first 28 and a second 30 strand of adhesive means. The location and dimensions of the first 28 and second 30 strand of adhesive means provides improved fastening of the guard 10 to the underwear of the wearer.

13 Claims, 3 Drawing Sheets

OTHER PUBLICATIONS

PCT/IPEA/409.
Decision on Grant Patent for Invention in RU 2008125053/14(030359) dated Jun. 15, 2009, and an English Translation thereof.

English-language translation of a Notice of Reasons for Rejection dated Nov. 2, 2010 issued in corresponding Japanese Patent Application No. 2008-541104.

* cited by examiner

MALE INCONTINENCE PRODUCT

TECHNICAL FIELD

The present invention concerns an incontinence guard for men. The incontinence guard is disposable, i.e. it is intended for single use, and comprises a liquid-permeable topsheet, a liquid-impermeable backsheet and an absorbent core located therebetween. More specifically, the invention concerns an incontinence guard having improved fastening to the underwear of the wearer.

BACKGROUND OF THE INVENTION

Light incontinence causes sufferers to involuntarily leak urine, and is a disability which is generally hidden. The problem and its causes are different between men and women. Many men who suffer from prostate problems also suffer from light incontinence. For instance, many men who have had prostate operations have encountered problems with light incontinence. Due to the anatomical differences between men and women, and the differences in the nature of the incontinence, incontinence guards have been specially designed for male users.

A typical male incontinence guard is shown in German utility model DE 298 21 849. It has a shape which is wider at the front of the guard and tapers towards the rear edge of the guard. Such an incontinence guard is fitted inside the wearer's underwear and has the ability to enclose the wearer's penis (and sometimes scrotum). The guard illustrated in DE 298 21 849 comprises three adhesive patches for fixing to the wearer's underwear.

U.S. Pat. No. 5,486,168 also describes a typical male incontinence guard.

WO 92/01431 also illustrates an incontinence guard (absorbent pad) for men. The guard has adhesive zones covered by a releasable cover sheet.

The technology and design of male incontinence guards has often been based on absorbent articles intended primarily for female users, such as panty-liners, female incontinence guards and sanitary towels, as the female market for such products has traditionally been much larger. However, the present inventors have recognised that the solutions provided by articles intended for use by female wearers are not always best suited for application to male incontinence guards. In particular, articles intended for use by female wearers provide means for securing the article in the underwear of the wearer which are not always entirely suitable when attempting to secure articles intended for use by male wearers. This particular problem arises from the differences in the types of underwear, anatomical differences between the sexes, different positioning of the article during use and the differences in the design of the article for male and female wearers.

OBJECTS AND SUMMARY

There remains a need for an incontinence guard for use by men which can be firmly and securely fixed in the underwear of the user. As the incontinence guard is intended to be disposable, the cost of the components is also an important factor. A balance is therefore required between the effectiveness of the guard and the cost of its components.

The present disclosure relates to an incontinence guard for males who suffer mild incontinence. Particularly, the incontinence guard remains firmly and securely fixed in the underwear of the user, while minimising the use of expensive components.

A male incontinence guard has a transverse (x) and a longitudinal (y) direction. The guard is divided by a transverse dividing line into a front region with a front transverse edge and a rear region with a rear transverse edge. The guard tapers towards the rear transverse edge. The garment-facing surface of the guard comprises a first and a second strand of adhesive means. The first strand of adhesive means is located in the front region of the guard, and has its substantial extension in the transverse direction (x). The front transverse edge of the first strand is located between 5-40 mm from the front transverse edge of the guard, and the rear transverse edge of the first strand is located between 5-50 mm from the transverse dividing line of the guard. The first strand has an extension in the transverse direction (x) of 70-170 mm. The second strand of adhesive means is located in the rear region of the guard, and has its substantial extension in the longitudinal direction (y). The front transverse edge of the second strand is located between 5-50 mm from the transverse dividing line of the guard, and the rear transverse edge of the second strand is located between 5-50 mm from the rear transverse edge of the guard. The second strand has an extension in the transverse direction (x) of 5-60 mm.

In the male incontinence guard, the strands of adhesive means may be continuous. Alternatively, at least one of the strands of adhesive means is intermittent. If the strands are intermittent, the subregions of each strand of adhesive means extend substantially in the longitudinal direction of the guard. Each strand of adhesive means may be covered by separate releasable cover sheet before use.

DETAILED DESCRIPTION OF PREFERRED EMBODIMENTS

Figure 1:
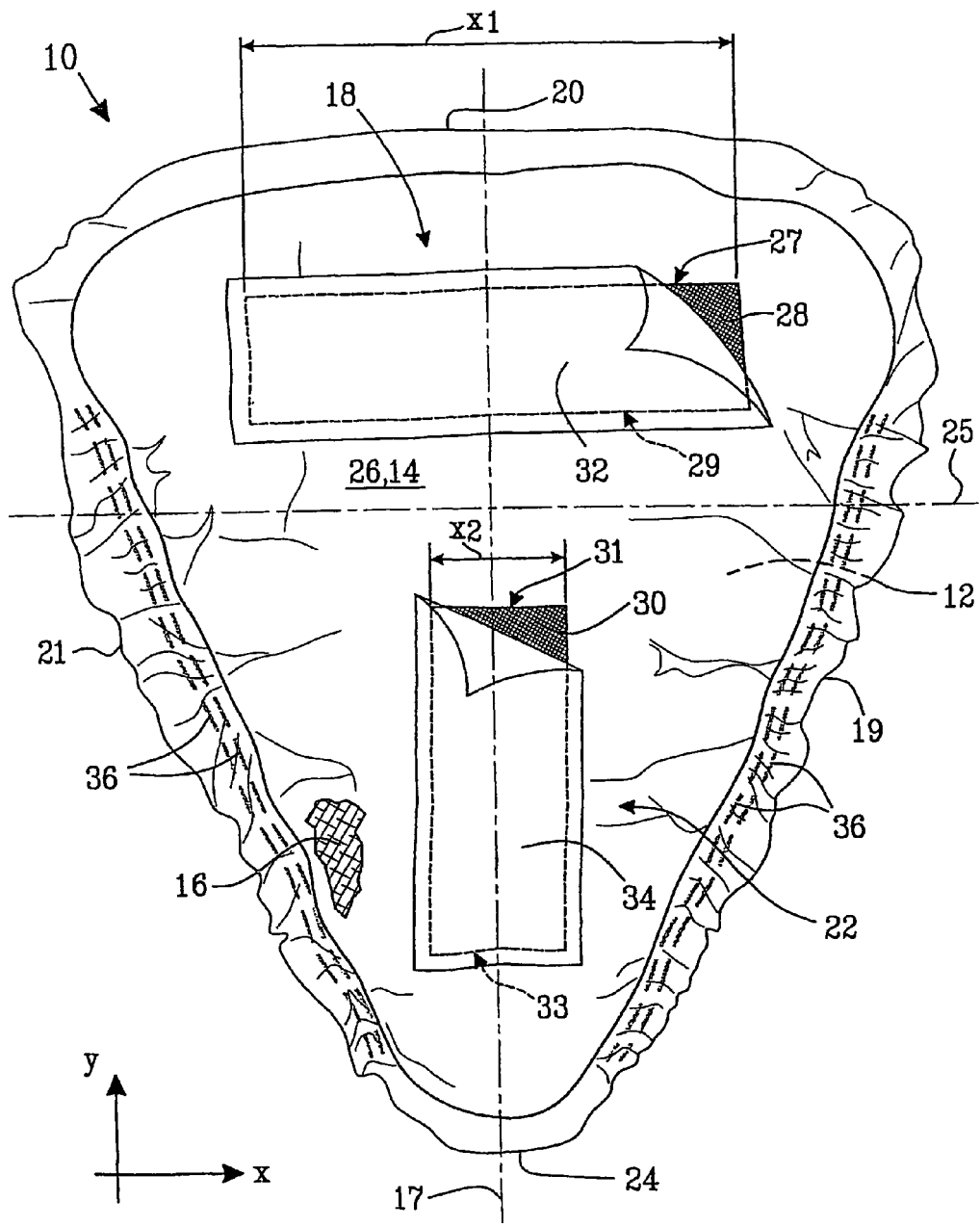
FIG. 1 shows an embodiment of an incontinence guard according to the present invention, seen from the garment-facing side.
Figure 2:
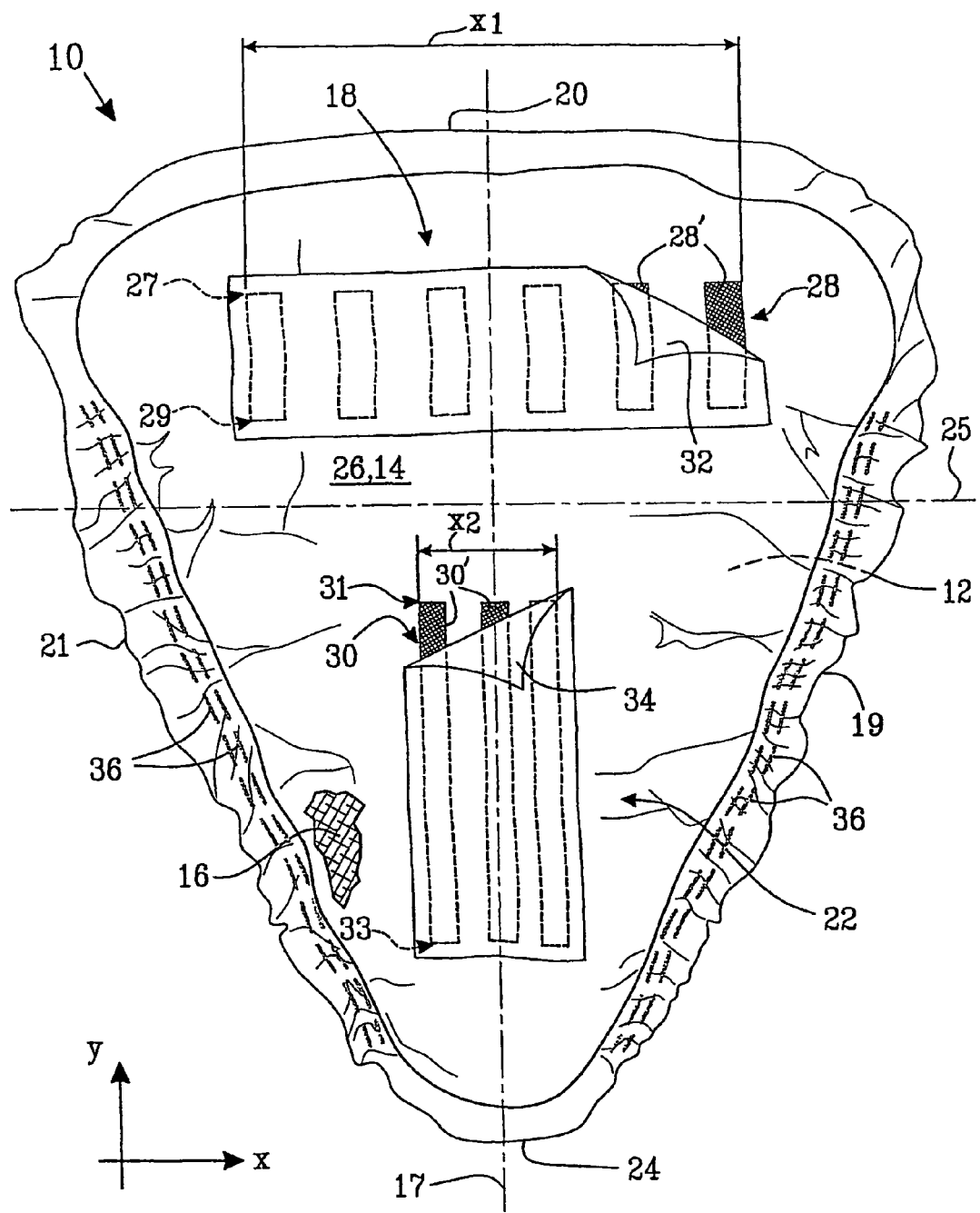
FIG. 2 shows an embodiment of an incontinence guard according to the present invention, seen from the garment-facing side, in which the strands of adhesive means are intermittent.

FIGS. 1-2 show embodiments of a male incontinence guard 10 according to the invention, seen from the garment-facing side. In these figures, the guard is laid out flat in all directions.

The guard 10 comprises a liquid-permeable topsheet 12, a liquid-impermeable backsheet 14 and an absorbent core 16 located therebetween. The liquid-permeable topsheet 12 can consist of a nonwoven material, e.g., a spunbond material of continuous filaments, a meltblown material, a bonded carded fibrous web or a perforated plastic film. Different types of laminates, e.g. laminates of non-woven material and plastic film may also be used. Materials which are suitable for the liquid-permeable topsheet 12 should be soft and non-irritating to the skin. Furthermore, the topsheet 12 can be different in different portions of the guard 10. The liquid-impermeable backsheet 14 may consist of a plastic film, a nonwoven material treated with a liquid impervious material or a hydrophobic nonwoven material which resists liquid penetration. Other types of liquid-barrier-materials may of course also be used as the liquid-impermeable backsheet 14, such as e.g. closed-cell plastic foams, various liquid-barrier laminates etc. It is preferable that the liquid-impermeable backsheet 14 is permeable to air and vapour.

The topsheet 12 and the backsheet 14 have a somewhat greater extension in the plane than the absorbent core 16 and extend outside the edges thereof. The topsheet 12 and the backsheet 14 are connected to each other within the projecting portions thereof, e.g., by gluing or welding by heat or ultrasound.

The absorbent core 16 can be of any conventional kind. Examples of commonly-occurring absorbent materials are cellulosic fluff pulp, tissue layers, highly absorbent polymers (so-called "superabsorbents"), absorbent foam materials, absorbent nonwovens or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. The thin absorbent bodies which are common in incontinence guards often comprise a compressed mixed or layered structure of cellulosic fluff pulp and superabsorbent.

The guard has a transverse (x) and a longitudinal (y) direction, and is symmetric about the longitudinal centre line 17. The guard is divided by a transverse dividing line 25 into a front region 18 with a front transverse edge 20 and a rear region 22 with a rear transverse edge 24.

The front region 18 is the region of the guard 10 which is intended to be located forward on the wearer when the guard 10 is being worn. The front region 18 is defined on one side by the front transverse edge 20, on two opposite sides by the longitudinal edges 19, 21 of the guard 10 and on the remaining side by the transverse dividing line 25 of the guard 10. The front region 18 extends in the longitudinal direction (y) a distance of up to 140 mm, preferably up to 120 mm, most preferably up to 100 mm from the front transverse edge 20.

The guard 10 further comprises a rear region 22 with a rear transverse edge 24. The rear region 22 is the region of the guard 10 which is intended to be located rearward on the wearer when the guard 10 is being worn. The rear region 22 is defined on one side by the rear transverse edge 24, on two opposite sides by the longitudinal edges 19, 21 of the guard and on the remaining side by the transverse dividing line 25 of the guard 10. The rear region 22 extends in the longitudinal direction (y) a distance of up to 200 mm, preferably up to 175 mm, most preferably up to 150 mm from the rear transverse edge 24.

The transition between the front or rear edge 20, 24 and an adjoining longitudinal edge 19, 21 may be clear from the shape of the guard. If not, it may be determined by drawing a tangent to the edge of the guard, and calculating the angle that this tangent makes with the transverse direction (x). As the tangent is moved to different points along the edge of the article, the angle it makes with the transverse direction (x) will vary. The transition between the front or rear edge 20, 24 and an adjoining longitudinal edge 19, 21 is that point at which the derivative of the angle between the tangent and the transverse direction with respect to the transverse direction (x) is greatest.

The guard 10 tapers towards the rear transverse edge 24. The guard 10 may therefore be essentially triangular or essentially isosceles trapezoid in form when fully extended in all directions. The word "essentially" in this context means that, for instance, the corners of the guard may be rounded, or that the edges of the guard may not be completely linear, but that the guard has the general form described above. The tapered shape allows the guard 10 to fit comfortably in the groin region of a male wearer.

The liquid-impermeable backsheet 14 of the guard 10 has a garment-facing surface 26, which is the surface which makes contact with the underwear of the user when the guard is being worn. This garment-facing surface 26 has two strands of adhesive means—a first strand 28 and a second strand 30.

According to one aspect, the adhesive means is a pressure-sensitive adhesive. According to a further aspect, the adhesive is a hot melt adhesive. Even more desirably, the adhesive is a pressure-sensitive holt melt adhesive. The adhesive may be cured by UV-radiation, as described in PCT/SE2004/002058.

The adhesive can be any of a large number of pressure-sensitive adhesives that are commercially available, including the cold, pressure-sensitive adhesives such as the acrylate adhesives, generally combined with tackifiers such as polyterpenes, or the rapid-setting thermoplastic adhesives (or hot melt adhesives) such as styrene and butadiene copolymers. Other ingredients such as fillers, antioxidants and pigments may be included. The adhesive may also comprise a double faced adhesive tape or another type of adhesive.

The surface weight of the adhesive disposed on the external, garment-facing surface or layer of the guard 10 may vary, for example in dependence on the specific adhesive used, but will be substantially 40 g/m$^2$ or lower because larger amounts may cause problems of too high adhesive forces when attached to the user's undergarment. A surface weight of between about 15 and 40 g/m$^2$ of adhesive will generally be used. Such an amount will also allow commercially effective production.

The first strand 28 of adhesive is located in the front region 18 of the guard 10, and has its substantial extension in the transverse direction (x) of the guard 10. The front transverse edge 27 of the first strand 28, i.e. that edge which is closest to the front transverse edge of the guard 10, is located between 5-40 mm, preferably 10-30 mm, more preferably 20-25 mm, from said edge 20. The rear transverse edge 29 of the first strand 28, i.e. that edge which is closest to the rear transverse edge 24 of the guard 10, is located between 5-50 mm, preferably 15-40 mm, more preferably 20-35 mm, from the transverse dividing line 25 of the guard 10. The first strand 28 has an extension x1 in the transverse direction (x) of 70-170 mm, preferably 90-130 mm, more preferably 100-120 mm, wherein the first strand 28 is centred in the transverse direction relative to the longitudinal centre line 17 of the guard 10.

The second strand 30 of adhesive is located in the rear region 22 of the guard 10 and has its substantial extension in the longitudinal direction (y). The front transverse edge 31 of the second strand 30, i.e. that edge which is closest to the front transverse edge 20 of the guard 10, is located between 5-50 mm, preferably 10-35 mm, more preferably 20-30 mm from the transverse dividing line 25 of the guard 10. The rear transverse edge 33 of the second strand 30, i.e. that edge which is closest to the rear transverse edge 24 of the guard 10, is located between 5-50 mm, preferably 10-40 mm, more preferably 15-30 mm, from said edge 24. The second strand 30 has an extension x2 in the transverse direction (x) of 5-60 mm, preferably 30-50 mm, more preferably 50 mm, wherein the second strand 30 is centred in the transverse direction relative to the longitudinal centre line 17 of the guard 10.

Incontinence guards in which the strands of adhesive do not meet the requirements as to their dimensions and location will not meet the requirements of secure fastening to the underwear of the wearer. For example, if the first strand 28 of adhesive does not lie within the stated distances from the front transverse edge 20 or the transverse dividing line 25 of the guard 10, the front region 18 of the guard will not be sufficiently fastened to the underwear of the wearer. Likewise, if the extension x1 of this first strand 28 of adhesive in the transverse direction is less than the stated extensions, the longitudinal edges 19, 21 of the incontinence guard 10 will not be sufficiently fastened to the underwear of the wearer in the front half of the guard. Similar reasoning can be applied for the second strand 30 of adhesive in the rear region 22 of the guard.

In the embodiment shown in FIG. 1, the strands 28, 30 of adhesive are continuous.

In the embodiment shown in FIG. 2, at least one of the strands 28, 30 of adhesive is intermittent. This provides the guard with substantially the same adhesive properties as the previously-described embodiment, yet allows the total amount of adhesive to be reduced. In this embodiment, the subregions 28', 30' of each strand 28, 30 of adhesive extend substantially in the longitudinal direction (y) of the guard 10. In this way, automated application of adhesive is made easier, as all the subregions are aligned.

Figure 3:
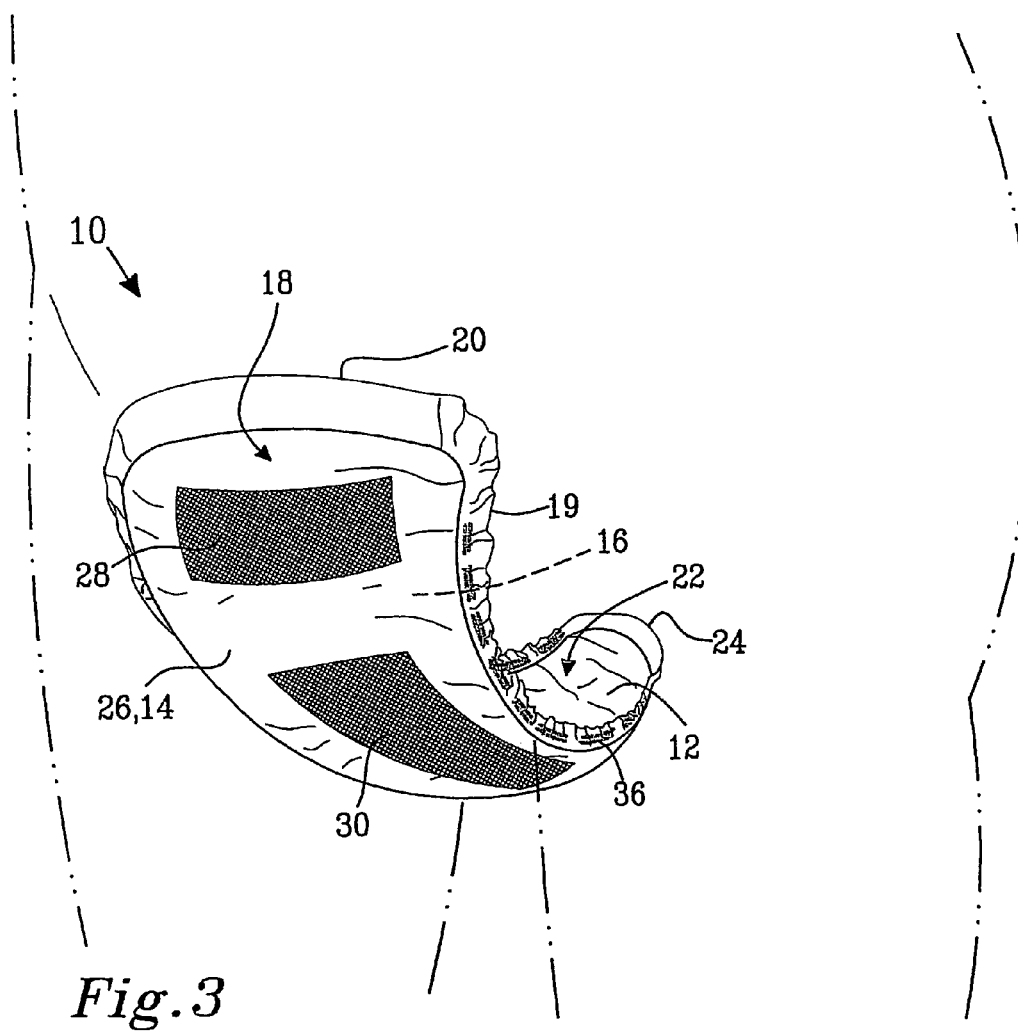
FIG. 3 shows a three-dimensional view of an incontinence guard according to the present invention in a user-like configuration.

Pre-stretched elastic devices 36 of mutually equal lengths may be attached in the longitudinal edges 19, 21 of the guard 10. The elastic devices 36 may, for instance, be in the form of elastic threads, bands or the like. The use of elastic foam material is also conceivable. The elastic devices 36 are preferably glued to one or to both of the backsheet or topsheet 12, 14. The elastic devices may be placed at any desired distance from the longitudinal edges 19, 21, and the area of overlap of the backsheet 12 and topsheet 14 at the longitudinal edges can have any desired size. The elastic devices 36 help the guard 10 to form a basin-like shape which encloses the genitals of the wearer, helping to maintain a close fit. In one variant of the inventive guard, it is conceivable to provide the guard with cross-elastication (i.e. in the transverse direction), so that the guard will also bend around a longitudinal axis. The use of elastic devices to provide a basin-like shape is further discussed in U.S. Pat. No. 5,486,168 and is illustrated in FIG. 3.

To protect the adhesive from dirt and damage, and to prevent it adhering before it is to be used, each strand 28, 30 of adhesive is covered by separate releasable cover sheets 32, 34 before use (see FIGS. 1 and 2). The releasable cover sheets are also used to prevent the adhesive from drying out before use. Providing two separate releasable cover sheets 32, 34 allows greater flexibility in the arrangement of the adhesive, and minimises the use of this expensive material as compared to a single releasable cover sheet covering both strands of adhesive. Such a releasable cover sheet may be made of a paper for example that has been treated so as to be readily releasable from the adhesive, e.g. a paper strip treated with silicone The present invention should not be limited by the above embodiments and the enclosed figures. Rather, the scope of the protection is determined by the enclosed claims and equivalents thereof.

The invention claimed is:

1. A male incontinence guard, comprising a transverse and a longitudinal direction, said guard being divided by a transverse dividing line into a front region with a front transverse edge and a rear region with a rear transverse edge, said guard having an essentially triangular shape and tapering towards the rear transverse edge so that the front region is wider in the transverse direction than the rear region, a garment-facing surface of the guard comprises a first and a second strand of adhesive, the first and second strands being on different sides of the transverse dividing line such that the first and second strands are separated from each other, said first strand of adhesive being located in the front region of the guard, said first strand extending in the transverse direction more than the first strand extends in the longitudinal direction, a front transverse edge of the first strand being located between 5-40 mm from the front transverse edge of the guard, and a rear transverse edge of the first strand being located between 5-50 mm from the transverse dividing line of the guard, said first strand having an extension in the transverse direction of 70-170 mm;

said second strand of adhesive being located in the rear region of the guard, said second strand extending in the longitudinal direction more than the second strand extends in the transverse direction, a front transverse edge of the second strand being located between 5-50 mm from the transverse dividing line of the guard, and a rear transverse edge of the second strand being located between 5-50 mm from the rear transverse edge of the guard, said second strand having an extension in the transverse direction of 5-60 mm;

wherein the rear transverse edge of the second strand is the farthest extent rearward in the longitudinal direction of any strand of adhesive in the rear region of the article, and the length of the rear transverse edge of the second strand is less than the length of the rear transverse edge of the first strand.

2. The male incontinence guard according to claim 1, wherein the strands of adhesive are continuous.

3. The male incontinence guard according to claim 1, wherein at least one of the strands of adhesive comprises intermittent subregions.

4. The male incontinence guard according to claim 3, wherein the subregions extend substantially in the longitudinal direction of the guard.

5. The male incontinence guard according to claim 1, wherein each strand of adhesive is covered by a separate releasable cover sheet before use.

6. The male incontinence guard according to claim 1, wherein the first and second strands of adhesive are the only strands of adhesive on the garment-facing surface of the guard.

7. The male incontinence guard according to claim 1, wherein the second strand of adhesive is substantially rectangular in shape.

8. The male incontinence guard according to claim 1, further comprising at least one elastic device attached to each longitudinal edge of the guard.

9. The male incontinence guard according to claim 8, wherein the at least one elastic device attached to each longitudinal edge of the guard is adapted to form the guard into a basin-like shape.

10. The male incontinence guard according to claim 1, wherein the first and second strands of adhesive are substantially rectangular in shape, wherein the first and second strands of adhesive are continuous, wherein the first and second strands of adhesive are the only strands of adhesive on the garment-facing surface of the guard.

11. The male incontinence guard according to claim 1, wherein the first strand of adhesive comprises intermittent subregions, wherein the subregions are parallel and rectangular, each subregion extending in the longitudinal direction more than each subregion extends in the transverse direction.

12. The male incontinence guard according to claim 11, wherein the second strand of adhesive comprises intermittent subregions, wherein the subregions are parallel and rectangular, each subregion extending in the longitudinal direction more than each subregion extends in the transverse direction.

13. The male incontinence guard according to claim 1, wherein the second strand of adhesive comprises intermittent subregions, wherein the subregions are parallel and rectangular, each subregion extending in the longitudinal direction more than each subregion extends in the transverse direction.

* * * * *